(12) United States Patent
Chadwick et al.

(10) Patent No.: US 7,437,959 B1
(45) Date of Patent: Oct. 21, 2008

(54) IN-WATER HULL CLEANING SAMPLING DEVICE

(75) Inventors: David Bartholomew Chadwick, San Diego, CA (US); Ignacio Rivera-Duarte, San Diego, CA (US); Robert Martin Cook, Escondido, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 247 days.

(21) Appl. No.: 11/417,282

(22) Filed: May 1, 2006

(51) Int. Cl.
*G01N 1/04* (2006.01)
*B63B 59/06* (2006.01)

(52) U.S. Cl. .............. 73/864.56; 73/863; 73/864; 73/864.34; 73/864.41; 114/222

(58) Field of Classification Search .......... 73/863, 73/864, 864.34, 864.41, 864.56; 114/222
See application file for complete search history.

(56) References Cited

U.S. PATENT DOCUMENTS

| | | | |
|---|---|---|---|
| 3,859,948 A * | 1/1975 | Romano et al. ........... | 114/222 |
| 3,946,692 A * | 3/1976 | Sierra et al. ............. | 114/222 |
| 4,574,722 A * | 3/1986 | Orita et al. .............. | 114/222 |
| 4,809,383 A * | 3/1989 | Urakami ................. | 15/98 |
| 4,838,193 A * | 6/1989 | van der Tak ............. | 114/222 |
| 4,926,957 A * | 5/1990 | Urakami ................. | 180/164 |
| 4,997,052 A * | 3/1991 | Urakami ................. | 180/164 |
| 5,007,210 A * | 4/1991 | Urakami ................. | 451/92 |
| 6,070,547 A * | 6/2000 | Achord .................. | 114/222 |
| 7,337,684 B1 * | 3/2008 | Lewis ................... | 73/864.41 |

FOREIGN PATENT DOCUMENTS

GB    2135571 A * 9/1984 ............. 114/222

* cited by examiner

*Primary Examiner*—Daniel S Larkin
(74) *Attorney, Agent, or Firm*—Kyle Eppele; Peter A. Lipovsky; Ryan J. Friedl

(57) ABSTRACT

An In-Water Hull Cleaning Sampling Device includes a sampling chamber, a drive shaft housing, a drive shaft sealing membrane, a drive shaft, a spring retainer, a pressure spring, a cleaning pad, a mechanical drive device and a chamber sealing means. The sampling chamber further includes a chamber sealing membrane coupled to a base; and a chamber wall coupled to the base and a chamber ceiling.

18 Claims, 11 Drawing Sheets

IN-WATER HULL CLEANING SAMPLING DEVICE

FEDERALLY SPONSORED RESEARCH AND DEVELOPMENT

This invention (Navy Case No. 98055) is assigned to the United States Government and is available for licensing for commercial purposes. Licensing and technical inquiries may be directed to the Office of Research and Technical Applications, Space and Naval Warfare Systems Center, San Diego, Code 2112, San Diego, Calif., 92152; voice (619) 553-2778; email T2@spawar.navy.mil. Reference Navy Case Number 98055.

BACKGROUND

The In-Water Hull Cleaning Sampling Device is generally in the field of environmental safety.

Typical cleaning methods of watercraft use abrasive materials that rub against watercraft hulls, which are usually covered in anti-fouling coatings. Anti-fouling coatings typically comprise a major source of copper, zinc and other toxins in coastal waterways.

A need exists for tools to help sample the amount of contaminants released as particles from watercraft and deposited in the environment when typical cleaning methods are used on watercraft hulls that are covered in anti-fouling coatings.

DETAILED DESCRIPTION

Described herein is In-Water Hull Cleaning Sampling Device.

DEFINITIONS

The following acronyms are used herein:

Acronym(s):

IWHCS—In-Water Hull Cleaning Sampling

The In-Water Hull Cleaning Sampling Device (IWHCS Device) includes a cleaning pad, drive shaft, pressure spring, mechanical drive means, sampling chamber and chamber sealing membrane. The IWHCS device provides a simple apparatus for sampling contaminants in particles by simulating in-water hull cleaning below the waterline (i.e., underwater). Several exemplary embodiments of the IWHCS device are described hereinbelow.

Figure 1:
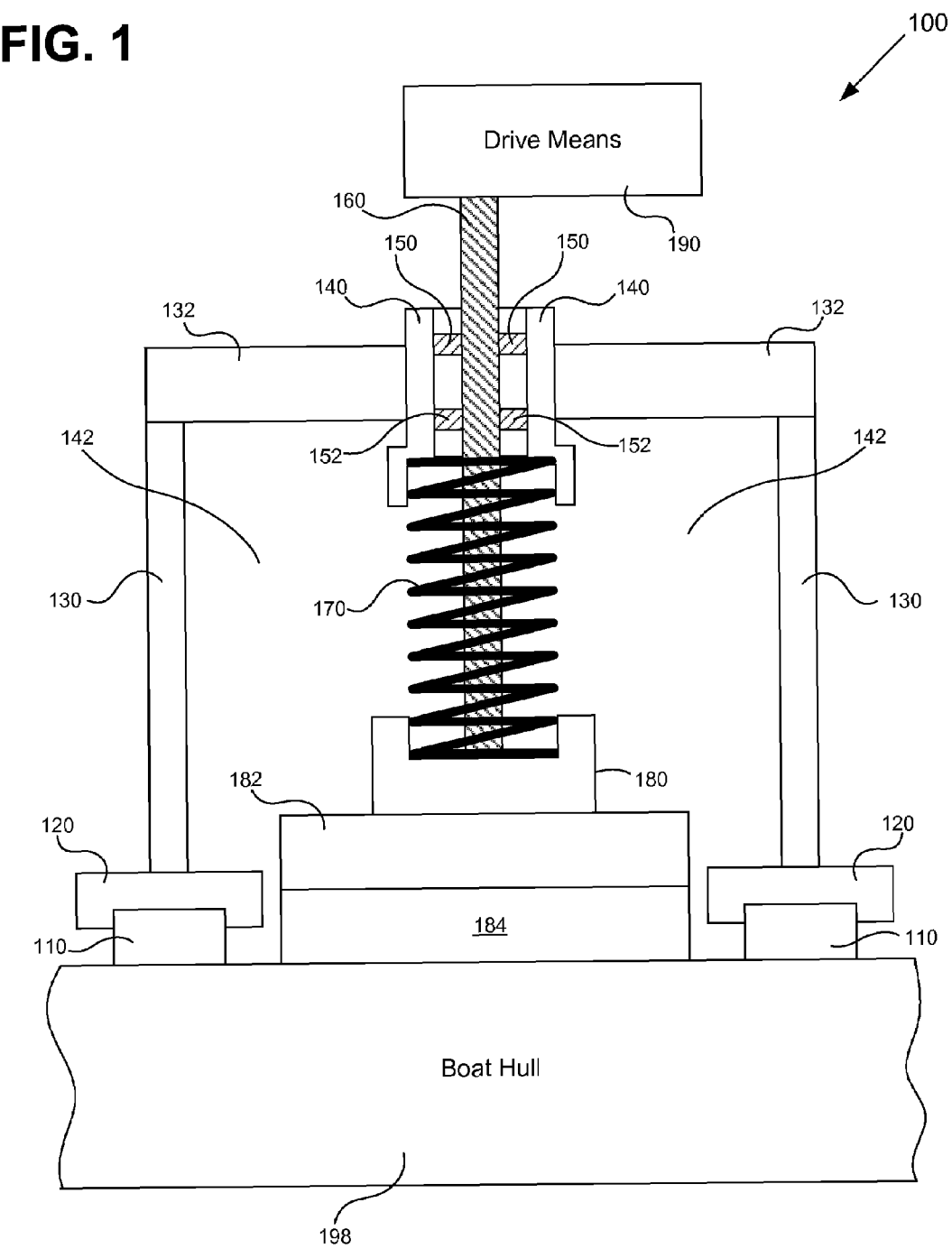
FIG. 1 is a side view of one embodiment of an in-water hull cleaning sampling device.

FIG. 1 is a side view of one embodiment of an in-water hull cleaning sampling device. As shown in FIG. 1, IWHCS device 100 includes chamber sealing membrane 110, base 120, chamber wall 130, chamber ceiling 132, drive shaft housing 140, sampling chamber 142, upper drive shaft sealing membrane 150, lower drive shaft sealing membrane 152, drive shaft 160, pressure spring 170, spring retainer 180, cleaning pad retainer 182, cleaning pad 184 and mechanical drive means 190. Sampling chamber 142 is a watertight enclosure partially defined by chamber sealing membrane 110, base 120, chamber wall 130 and chamber ceiling 132. In one embodiment, sampling chamber 142 has a cylindrical configuration. Thus, chamber ceiling 132 has a circular configuration; and chamber wall 130, base 120 and membrane 110 have cylindrical configurations. In one embodiment, sampling chamber 142 has an elliptical configuration. Thus, chamber ceiling 132, chamber wall 130, base 120 and chamber sealing membrane 110 have elliptical configurations. Those of ordinary skill in the art shall recognize that other configurations can be used with the present IWHCS device 100 without departing from the scope or spirit of the present IWHCS device 100. Other exemplary configurations include square, rectangular and polygonal.

Chamber sealing membrane 110 comprises a watertight material capable of forming a watertight seal. In one embodiment, chamber sealing membrane 110 comprises a gasket. In one embodiment, chamber sealing membrane 110 comprises a rubber O-ring. Chamber sealing membrane 110 is adapted to form a watertight seal when applied flush against boat hull 198. Thus, sampling chamber 142 is substantially sealed from ambient water surrounding IWHCS device 100.

Base 120 is operatively coupled to chamber sealing membrane 110 in a watertight manner. Base 120 is capable of retaining chamber sealing membrane 110. Base 120 comprises a watertight material. In one embodiment, base 120 comprises a plastic material. In one embodiment, base 120 comprises a polycarbonate material. In one embodiment, base 120 comprises fiberglass material. Those of ordinary skill in the art shall recognize that other watertight materials that are compatible with chemical sampling protocols can be used with the present IWHCS device 100 without departing from the scope or spirit of the present IWHCS device 100.

Chamber wall 130 is operatively coupled to base 120 in a watertight manner. Chamber wall 130 comprises a watertight material. In one embodiment, chamber wall 130 comprises a plastic material. In one embodiment, chamber wall 130 comprises a polycarbonate material. In one embodiment, chamber wall 130 comprises fiberglass material. Those of ordinary skill in the art shall recognize that other watertight materials can be used with the present IWHCS device 100 without departing from the scope or spirit of the present IWHCS device 100.

Chamber ceiling 132 is operatively coupled to chamber wall 130 in a watertight manner. Chamber ceiling 132 comprises a watertight material. In one embodiment, chamber ceiling 132 comprises a plastic material. In one embodiment, chamber ceiling 132 comprises a polycarbonate material. In one embodiment, chamber ceiling 132 comprises fiberglass material. Those of ordinary skill in the art shall recognize that other watertight materials can be used with the present IWHCS device 100 without departing from the scope or spirit of the present IWHCS device 100.

Drive shaft housing 140 is operatively coupled to chamber ceiling 132 in a watertight manner. In one embodiment, drive shaft housing 140 forms a concentric cylinder substantially centered upon a central longitudinal axis of IWCHS device 100. Drive shaft housing 140 comprises a watertight material. In one embodiment, drive shaft housing 140 comprises a plastic material. In one embodiment, drive shaft housing 140 comprises a polycarbonate material. In one embodiment, drive shaft housing 140 comprises fiberglass material. In one embodiment, drive shaft housing 140 includes a flanged lip to help retain pressure spring 170. Those of ordinary skill in the art shall recognize that other watertight materials can be used with the present IWHCS device 100 without departing from the scope or spirit of the present IWHCS device 100.

Upper drive shaft sealing membrane 150 and lower drive shaft sealing membrane 152 are operatively coupled to drive shaft housing 140 in a watertight manner. In one embodiment, upper drive shaft sealing membrane 150 and lower drive shaft sealing membrane 152 each form a concentric cylinder substantially centered upon a central longitudinal axis of IWCHS device 100. Upper drive shaft sealing membrane 150 and lower drive shaft sealing membrane 152 are both adapted to retain drive shaft 160 along an axis of IWHCS device 100. Upper drive shaft sealing membrane 150 and lower drive shaft sealing membrane 152 comprise a watertight material capable of forming a watertight seal. In one embodiment, upper drive shaft sealing membrane 150 and lower drive shaft sealing membrane 152 comprise gaskets. In one embodiment, upper drive shaft sealing membrane 150 and lower drive shaft sealing membrane 152 comprise rubber O-rings.

Drive shaft 160 is retained by upper drive shaft sealing membrane 150 and lower drive shaft sealing membrane 152 within drive shaft housing 140 in a watertight manner. Drive shaft 160 is capable of rotating along a longitudinal axis of IWCHS device 100. In one embodiment, drive shaft 160 is situated substantially along a central longitudinal axis of IWCHS device 100. Drive shaft 160 is situated partially outside of sampling chamber 142 and partially within sampling chamber 142. Upper drive shaft sealing membrane 150 and lower drive shaft sealing membrane 152 are adapted to retain drive shaft 160. Upper drive shaft sealing membrane 150 and lower drive shaft sealing membrane 152 allow drive shaft 160 to rotate along a longitudinal axis while maintaining a watertight seal that prevents water outside of sampling chamber 142 to flow into sampling chamber 142 and water contained within sampling chamber 142 from flowing out of sampling chamber 142.

Spring retainer 180 is operatively coupled to drive shaft 160 so that spring retainer 180 rotates when drive shaft 160 rotates. Spring retainer 180 comprises a water resistant material or watertight material. In one embodiment, spring retainer 180 comprises a plastic material. Spring retainer 180 is adapted to retain one end of pressure spring 170 in place around a longitudinal axis of IWCHS device 100. In one embodiment, spring retainer 182 comprises a flanged disc, which helps retain pressure spring 170. In one embodiment, spring retainer 180 retains one end of pressure spring 170 so that pressure spring 170 is situated around drive shaft 160.

Pressure spring 170 is operatively coupled to drive shaft housing 140 and spring retainer 180. Pressure spring 170 is situated along the same longitudinal axis of drive shaft 160. Pressure spring 170 has a spring constant (k). Pressure spring 170 is selected so that its downward force (i.e., toward boat hull 198) simulates a desired pressure. Pressure spring 170 can be covered with a plastic film so that pressure spring 170 does not contact water. Those skilled in the art shall recognize that various springs can be selected as pressure spring 170 without departing from the scope and spirit of the IWCHS device.

Cleaning pad retainer 182 is operatively coupled to spring retainer 180 so that cleaning pad retainer 182 rotates when drive shaft 160 rotates. Cleaning pad retainer 182 comprises a water resistant material or watertight material. In one embodiment, cleaning pad retainer 182 comprises a plastic material. Cleaning pad retainer 182 is adapted to retain cleaning pad 184.

Cleaning pad 184 is operatively coupled to cleaning pad retainer 182 so that cleaning pad 184 rotates when drive shaft 160 rotates. Cleaning pad 184 comprises a material having an abrasive surface. In one embodiment, cleaning pad 184 comprises a stiff bristle brush. In one embodiment, cleaning pad 184 comprises a rotary-style scrub brush. In one embodiment, cleaning pad 184 comprises a soft scouring pad. In one embodiment, cleaning pad 184 comprises a grungy material. Cleaning pad 184 is adapted to simulate a cleaning tool used to clean watercraft hulls below the waterline.

Mechanical drive means 190 is operatively coupled to drive shaft 160. Mechanical drive means 190 is adapted to provide rotational force that rotates drive shaft 160 along a longitudinal axis of IWHCS device 100, which rotates cleaning pad 184 to simulate a cleaning motion. In one embodiment, mechanical drive means 190 is adapted to rotate drive shaft 160 substantially along a central longitudinal axis of IWHCS device 100. In one embodiment, mechanical drive means 190 comprises a motor. In one embodiment, mechanical drive means 190 comprises an electric motor. In one embodiment, mechanical drive means 190 comprises a battery-powered motor. In one embodiment, mechanical drive means 190 comprises a gasoline-powered motor. In one embodiment, mechanical drive means 190 comprises a manually-powered device. In one embodiment, mechanical drive means 190 comprises a hand crank. In one embodiment, mechanical drive means 190 comprises a foot pedal crank. In one embodiment, mechanical drive means 190 comprises a pneumatic pump. Those skilled in the art shall recognize that various mechanical means can be selected as mechanical drive means 190 without departing from the scope and spirit of the IWCHS device.

An exemplary operation of IWHCS device 100 of FIG. 1 is now described. IWHCS device 100 is adapted to simulate in-water hull cleaning. In the exemplary operation of IWHCS device 100, IWHCS device 100 is situated flush against boat hull 198. Pressure is applied so that chamber sealing membrane 110 maintains contact with boat hull 198, which prevents ambient water from entering sampling chamber 142. Pressure spring 170 provides pressure so that cleaning pad 184 is pressing against boat hull 198 with a force that approximately equals a force used to clean boat hull 198. Mechanical drive means 190 provides rotational force to drive shaft 160, which rotates cleaning pad 184. When cleaning pad 184 rotates against boat hull 198, cleaning pad 184 removes contaminants from boat hull 198. During simulated cleaning, contaminants from boat hull 198 migrate into sampling chamber 142 and cleaning pad 184.

Figure 2:
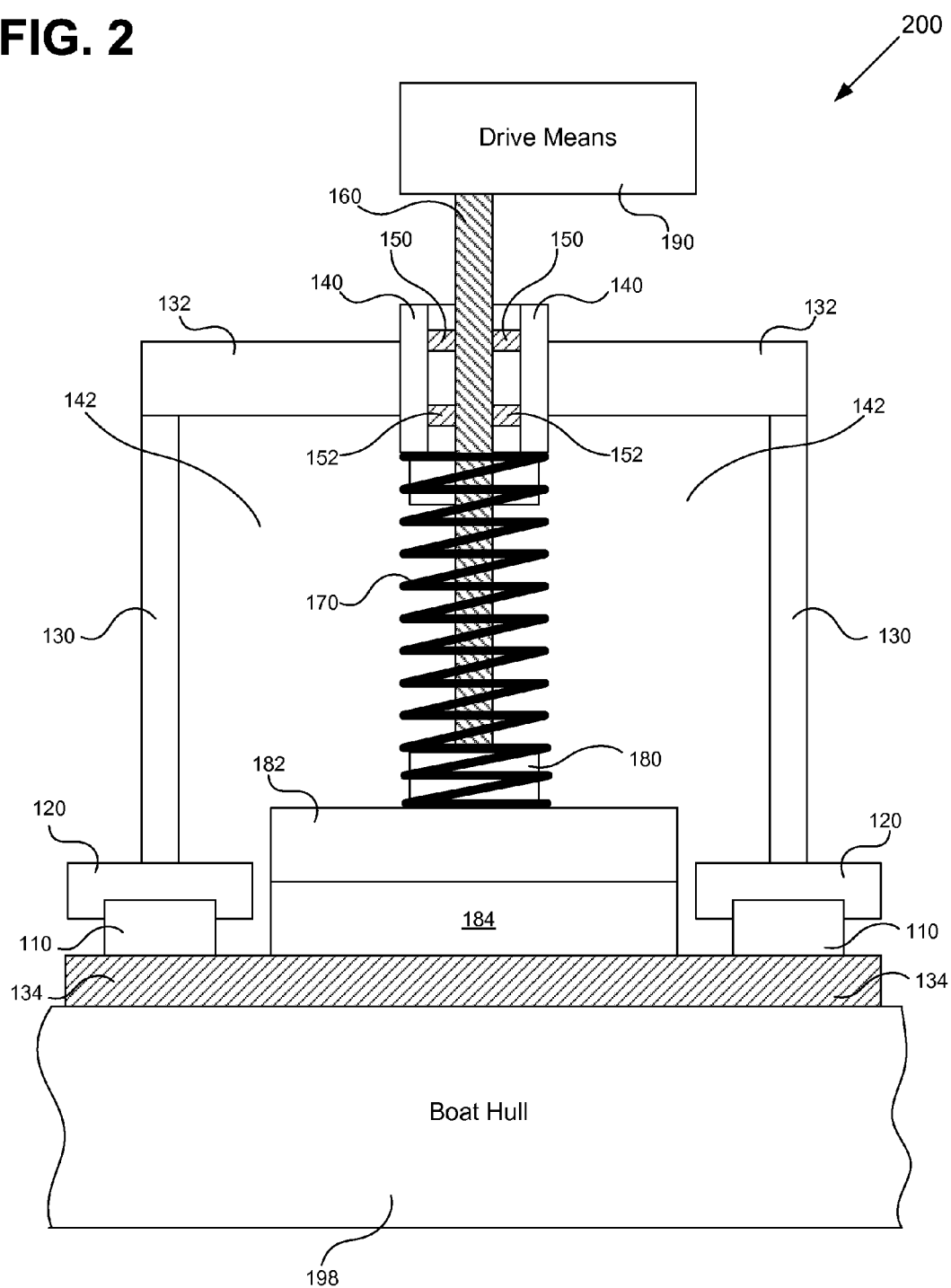
FIG. 2 is a side view of one embodiment of an in-water hull cleaning sampling device.

FIG. 2 is a side view of one embodiment of an in-water hull cleaning sampling device. IWHCS device 200 of FIG. 2 is substantially similar to IWHCS device 100 of FIG. 1, and thus, identical components are not described hereinagain. As shown in FIG. 2, IWHCS device 200 further comprises chamber sealing device 134. Chamber sealing device 134 comprises a substantially rigid, watertight material. In one embodiment, chamber sealing device 134 comprises a plastic material. In one embodiment, chamber sealing device 134 comprises a polycarbonate material. In one embodiment, chamber sealing device 134 comprises fiberglass material. Chamber sealing device 134 is operatively coupled to chamber sealing membrane 110. In one embodiment, chamber sealing device 134 is operatively coupled to chamber sealing membrane 110 via pressure applied on IWHCS device 200 toward boat hull 198. Chamber sealing device 134 is adapted to prevent water and contaminants from leaving sampling chamber 142 and prevent water from entering sampling chamber 142.

An exemplary operation of IWHCS device 200 of FIG. 2 is now described. After IWHCS device 200 simulates in-water hull cleaning of boat hull 198 (see above description with regard to IWHCS device 100 of FIG. 1), chamber sealing device 134 can be actuated to seal sampling chamber 142. In one embodiment, chamber sealing device 134 is manually slid between boat hull 198 and chamber sealing membrane 110. IWHCS device 200 can be removed from underwater and the contents of sampling chamber 142 can be removed for testing and measurement of contaminants.

Figure 3:
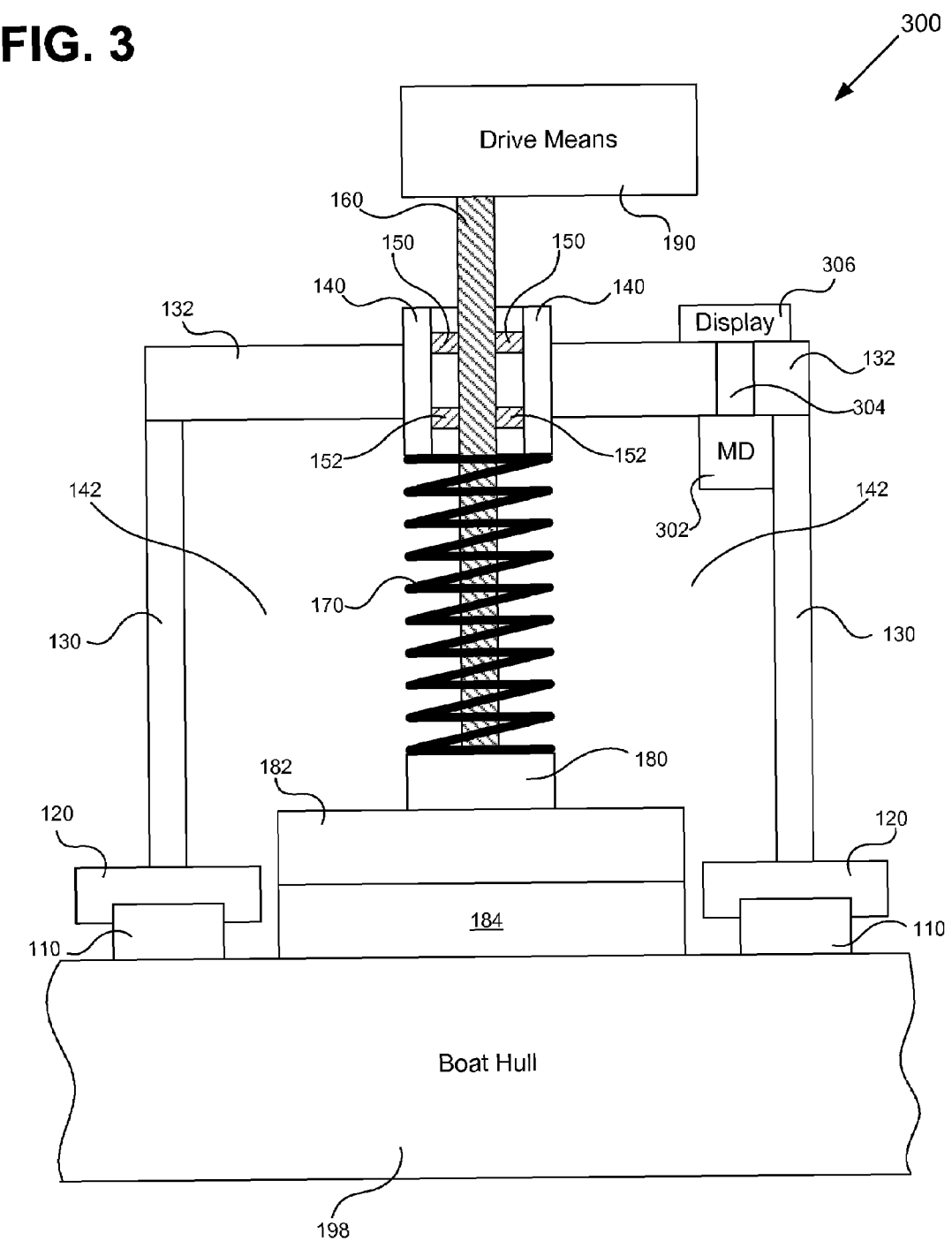
FIG. 3 is a side view of one embodiment of an in-water hull cleaning sampling device.

FIG. 3 is a side view of one embodiment of an in-water hull cleaning sampling device. IWHCS device 300 of FIG. 3 is substantially similar to IWHCS device 100 of FIG. 1, and thus, identical components are not described hereinagain. As shown in FIG. 3, IWHCS device 300 further comprises measurement device 302, measurement device link 304 and display 306. Measurement device 302 is situated within sampling chamber 142. In one embodiment, measurement device 302 is operatively coupled to chamber ceiling 132. Measurement device 302 is capable of analyzing the contents of sampling chamber 142. Measurement device 302 comprises at least one sensor. Exemplary sensors include turbidity, salinity, oxygenation, acidity, mercury, copper, pesticide and bacterial. In one embodiment, measurement device 302 comprises a turbidity sensor. In one embodiment, measurement device 302 comprises electrodes. In one embodiment, measurement device 302 includes a data storage means such as RAM, ROM, hard disk, flash memory.

As shown in FIG. 3, measurement device link 304 is operatively coupled to measurement device 302. Measurement device link 304 provides a means for information to be transmitted from measurement device 302 and display 306. In one embodiment, measurement device link 304 comprises insulated copper wiring. In one embodiment, measurement device link 304 comprises optical cable. In one embodiment, measurement device link 304 comprises a wireless radio frequency link. In one embodiment, measurement device link 304 is adjacent to chamber ceiling 132.

Display 306 is operatively coupled to measurement device link 304. Display 306 is capable of displaying information received from measurement device 302 via measurement device link 304. In one embodiment, display 306 comprises a digital LED. In one embodiment, display 306 comprises a digital LCD. In one embodiment, display 306 comprises an analog gauge. In one embodiment, display 306 comprises an acoustic speaker. In one embodiment, display 306 includes a data storage means such as RAM, ROM, hard disk, flash memory.

Figure 4:
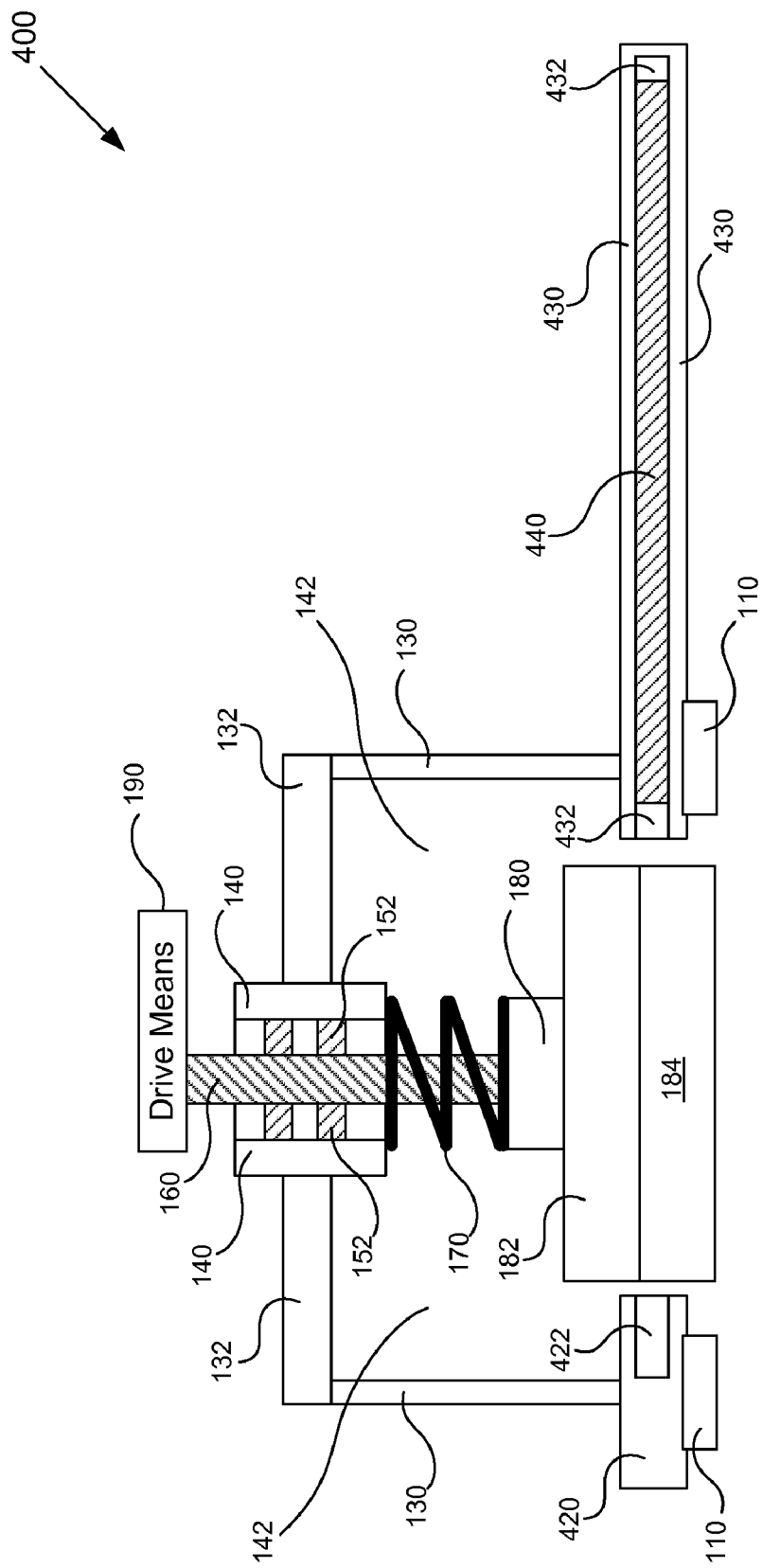
FIG. 4 is a side view of one embodiment of an in-water hull cleaning sampling device.

FIG. 4 is a side view of one embodiment of an in-water hull cleaning sampling device. IWHCS device 400 of FIG. 4 is substantially similar to IWHCS device 100 of FIG. 1, and thus, identical components are not described hereinagain. As shown in FIG. 4, IWHCS device 400 includes base 420, extended base 430 and chamber sealing slide panel 440. Base 420 is operatively coupled to chamber sealing membrane 110 in a watertight manner. Base 420 is capable of retaining chamber sealing membrane 110. Base 420 comprises a watertight material. Base aperture 422 is adapted to receive a proximal end of chamber sealing slide panel 440. Base aperture 422 is formed within base 420. Extended base 430 is operatively coupled to chamber sealing membrane 110 in a watertight manner. Base 430 is capable of retaining chamber sealing membrane 110. Extended base aperture 432 is formed within extended base 430. Extended base aperture 432 is adapted to snugly house chamber sealing slide panel 440. Extended base aperture 432 is adapted to allow chamber sealing slide panel 440 to move from within extended base 430 to be situated partially within base 420 and partially within extended base 430. Chamber sealing slide panel 440 comprises a watertight material. Chamber sealing slide panel 440 is adapted to form a watertight seal that encloses sampling chamber 142 when cleaning pad 184 is retracted into sampling chamber 142.

Figure 5:
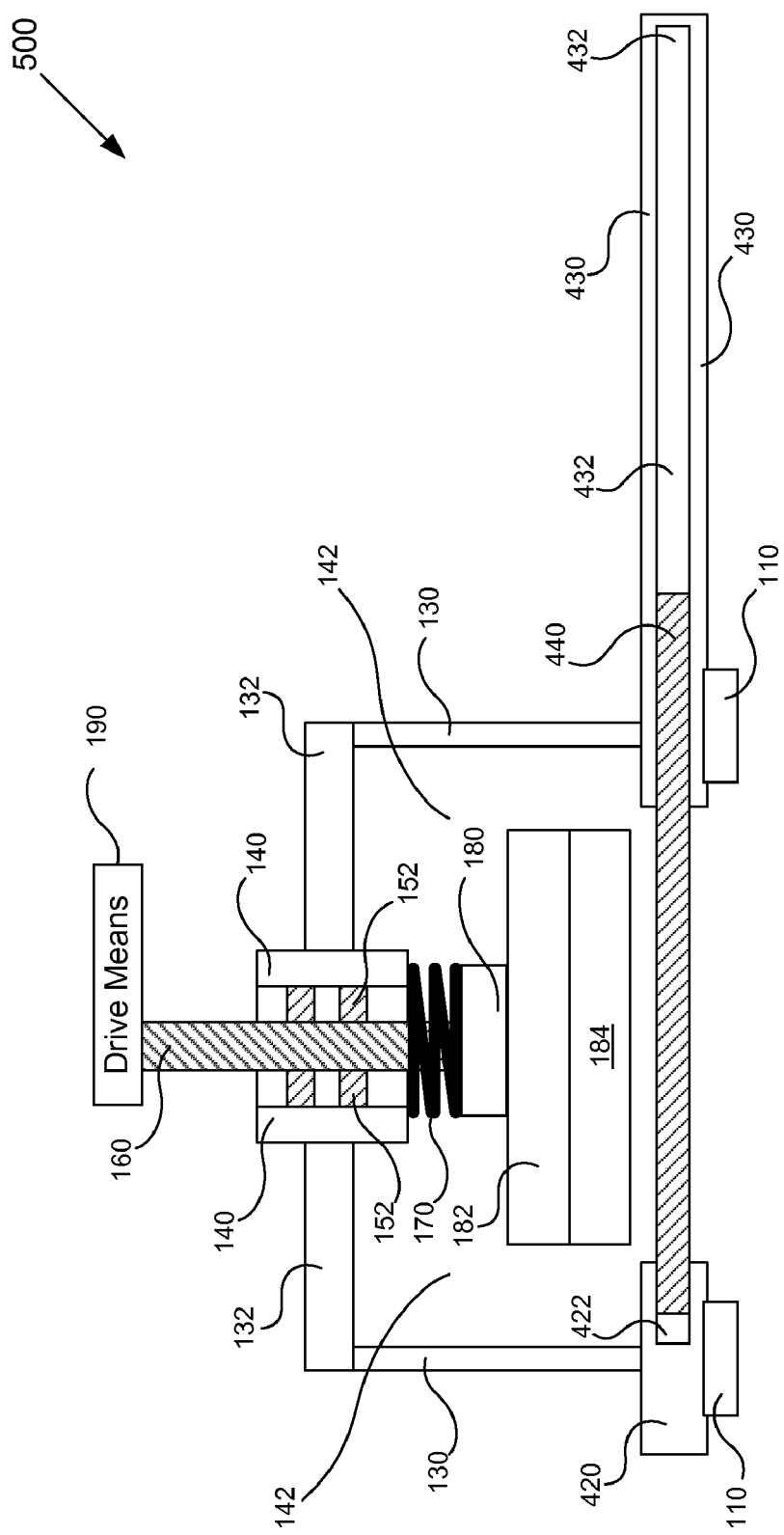
FIG. 5 is a side view of one embodiment of an in-water hull cleaning sampling device.

FIG. 5 is a side view of one embodiment of an in-water hull cleaning sampling device. IWHCS device 500 of FIG. 5 is substantially similar to IWHCS device 400 of FIG. 4, and thus, identical components are not described hereinagain. As shown in FIG. 5, cleaning pad 184 is retracted into sampling chamber 142, which is sealed by chamber sealing slide panel 440. In one embodiment, cleaning pad 184 is retracted by pulling drive shaft 160 upward (i.e., away from chamber ceiling 132). Chamber sealing slide panel 440 can be actuated using ordinary means in the art such as a spring lock and manual slide lever means.

Figure 6:
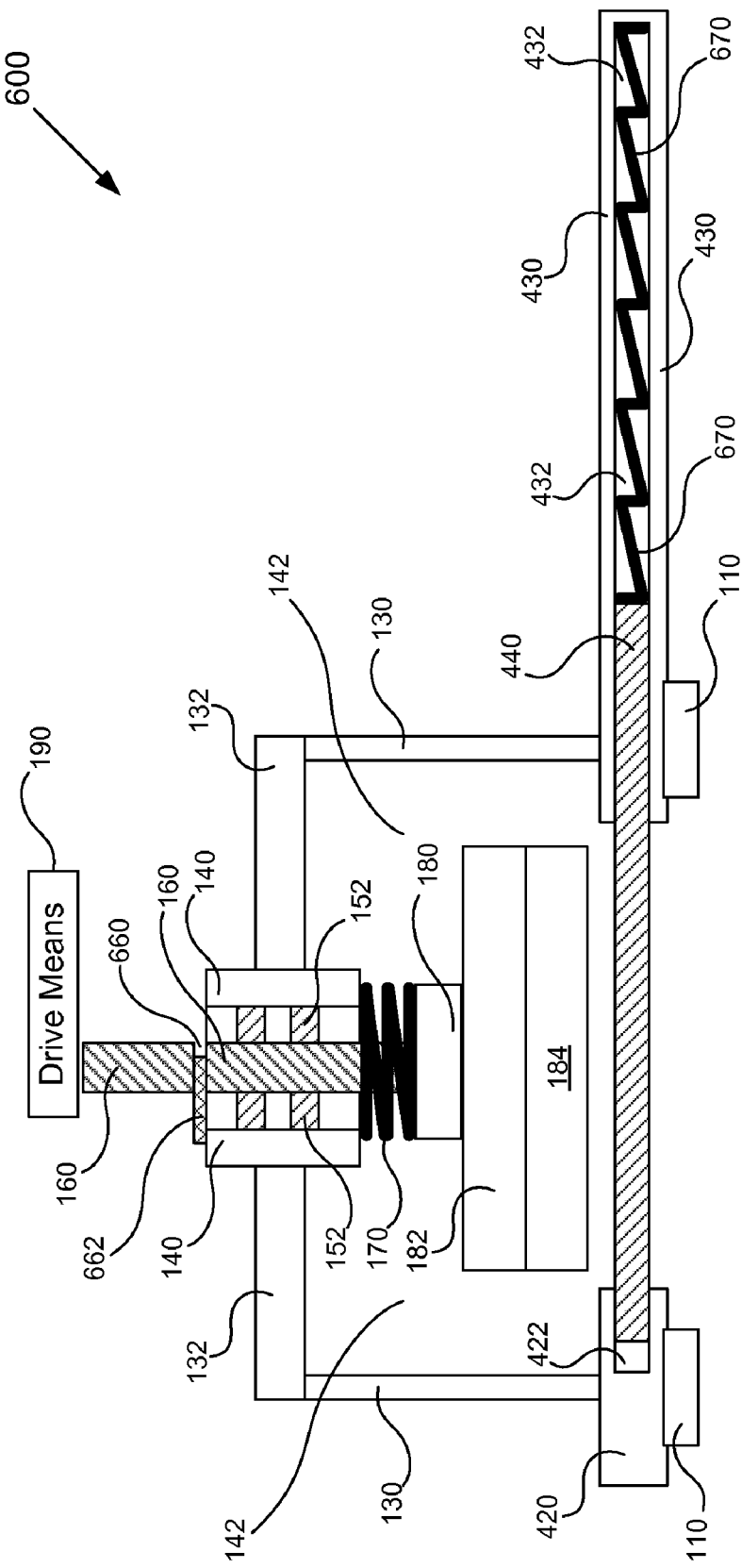
FIG. 6 is a side view of one embodiment of an in-water hull cleaning sampling device.

FIG. 6 is a side view of one embodiment of an in-water hull cleaning sampling device. FIG. 6 is a spring lock embodiment of the IWHCS device. IWHCS device 600 of FIG. 6 is substantially similar to IWHCS device 400 of FIG. 4, and thus, identical components are not described hereinagain. As shown in FIG. 6, cleaning pad 184 is retracted into sampling chamber 142. Cleaning pad 184 is locked in retracted position using drive shaft aperture 660 and drive shaft lock pin 662. Drive shaft aperture 660 is formed within drive shaft 160. Drive shaft aperture 660 is adapted to snugly receive drive shaft lock pin 662. When drive shaft lock pin 662 is situated within drive shaft aperture 660 and partially outside drive shaft aperture 660, cleaning pad 184 is locked in the retracted position.

As shown in FIG. 6, sampling chamber 142 is sealed by chamber sealing slide panel 440. Slide panel spring 670 forces chamber sealing slide panel 440 into base aperture 422 of base 420. When in sampling mode, chamber sealing slide panel 440 is locked into place by a mechanical lock located within extended base 440 (not shown in FIG. 6).

Figure 7:
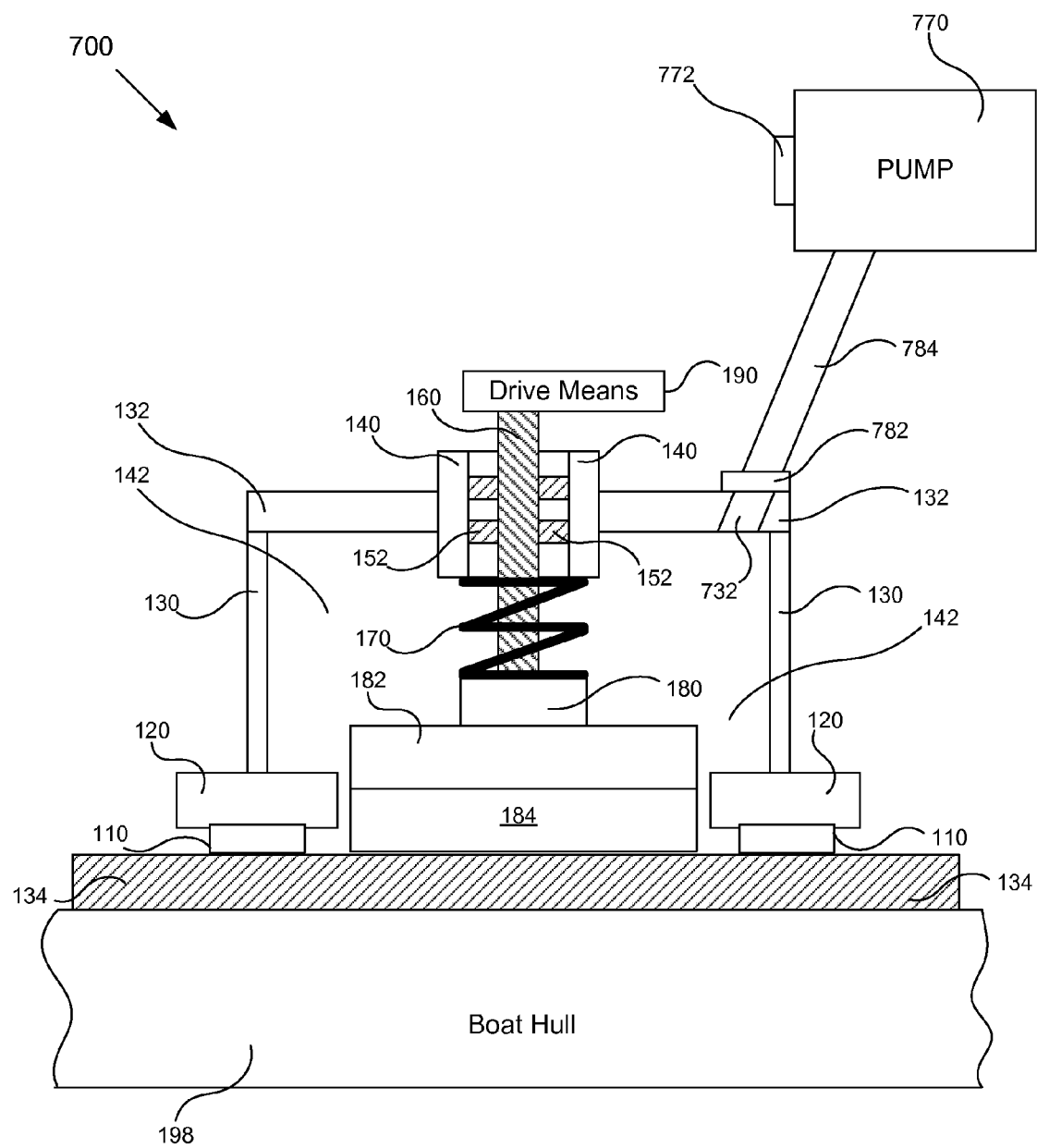
FIG. 7 is a side view of one embodiment of an in-water hull cleaning sampling device.

FIG. 7 is a side view of one embodiment of an in-water hull cleaning sampling device. FIG. 7 is a negative pressure embodiment of the IWHCS device. IWHCS device 700 of FIG. 7 is substantially similar to IWHCS device 100 of FIG. 1, and thus, identical components are not described hereinagain. As shown in FIG. 7, IWHCS device 700 includes pump 770, outtake valve 772, pump conduit 784, intake valve 782 and intake aperture 732. Intake aperture 732 is formed within chamber ceiling 132. Intake aperture 732 is adapted to facilitate the flow of water between sampling chamber 142 and pump conduit 784. Intake valve 782 is operatively coupled to chamber ceiling 132 and pump conduit 784. Intake valve 782 forms a watertight seal so that water does not flow between the exterior of sampling chamber 142 and the following: the interior of sampling chamber 142, intake aperture 732 and pump conduit 784. When intake valve 782 is open, water can flow between sampling chamber 142 and pump conduit 784 via intake aperture 732 given that the pressure differential is favorable for such flow. Pump conduit 784 is operatively coupled to intake valve 782. Pump conduit 784 is adapted to facilitate the flow of water to and from sampling chamber 142 via intake aperture 732 and intake valve 782.

As shown in FIG. 7, pump 770 is operatively coupled to pump conduit 784. Pump 770 is capable of pumping water into or out of sampling chamber 142 via pump conduit 784, valve 782 and intake aperture 732. Pump 770 is capable of creating a negative or positive pressure within sampling chamber 142 when intake valve 782 is open or partially open. Outtake valve 772 is operatively coupled to pump 770. Outtake valve 772 is capable of opening and closing. When water is pumped out of sampling chamber 142 via intake aperture 732, valve 782 and pump conduit 784, the water is expelled through outtake valve 772.

An exemplary operation of the negative pressure pump embodiment of IWHCS device 700 of FIG. 7 is now described. In the exemplary operation of IWHCS device 700, IWHCS device 700 is situated flush against a boat hull (not shown in FIG. 7, however, shown in FIG. 1 as boat hull 198). Pressure is applied so that chamber sealing membrane 110 maintains contact with the boat hull, which prevents ambient water from entering sampling chamber 142. Prior to simulating cleaning, pump 770 is activated to pull a small amount of water from sampling chamber 142 via intake aperture 732, intake valve 782, conduit 784 and outtake valve 772. Thus, a slight negative pressure is created within sampling chamber 142, which helps chamber sealing membrane 110 maintain a watertight seal. Then, simulated cleaning proceeds as described above with reference to the exemplary operation of IWHCS device 100 of FIG. 1

Figure 8:
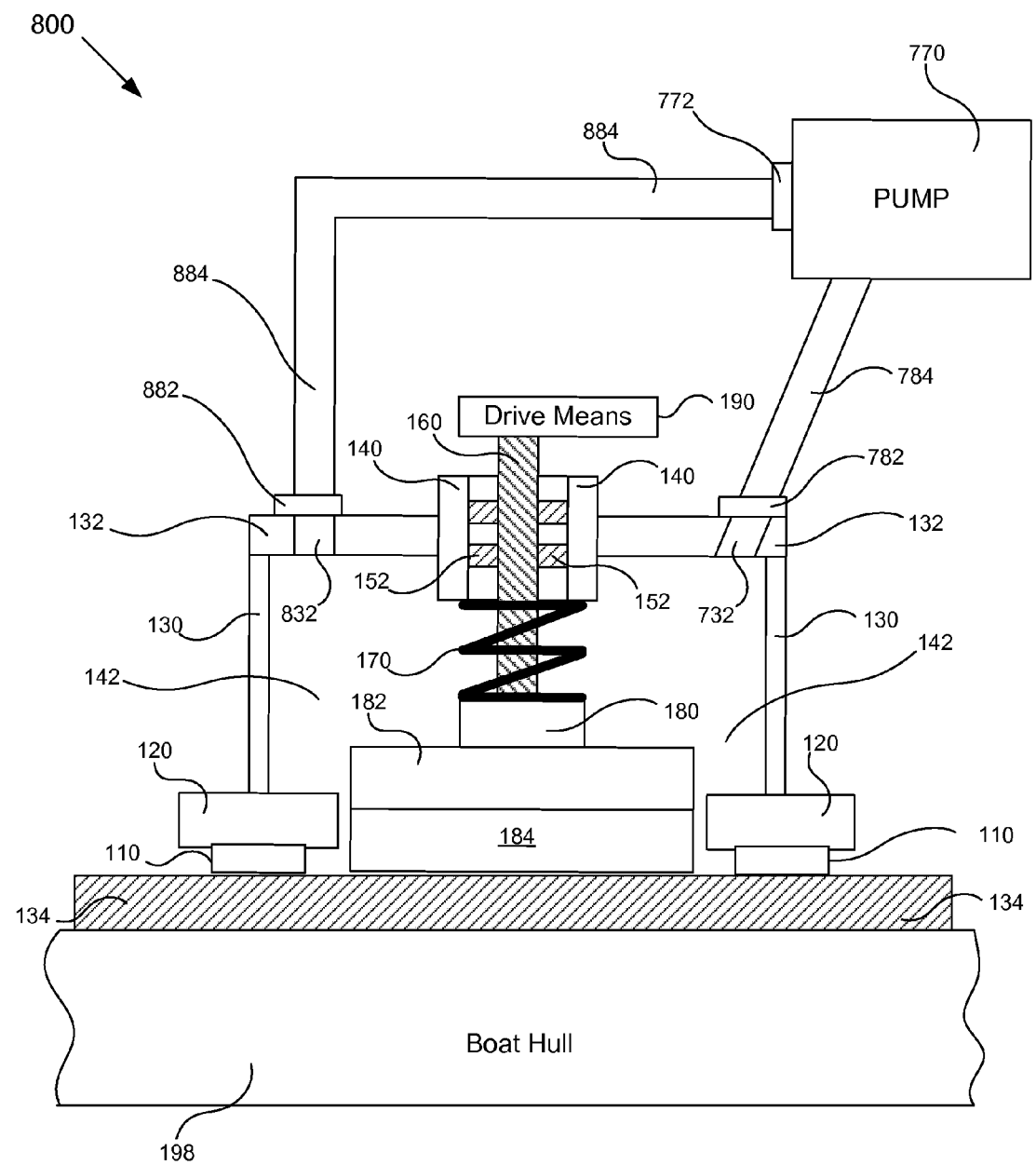
FIG. 8 is a side view of one embodiment of an in-water hull cleaning sampling device.

FIG. 8 is a side view of one embodiment of an in-water hull cleaning sampling device. FIG. 8 is a closed-loop pump embodiment of the IWHCS device, which provides recirculation of water contained within sampling chamber 142. The closed-loop pump embodiment provides increased probability of even distribution of contaminants that are suspended in water contained within sampling chamber 142, and thus, loss of contaminants when sealing sampling chamber 142 with chamber sealing device 134 or chamber sealing slide panel 440 (see FIGS. 4-6) is reduced. IWHCS device 800 of FIG. 8 is substantially similar to IWHCS device 100 of FIG. 1 and IWHCS device 700 of FIG. 7, and thus, identical components are not described hereinagain.

As shown in FIG. 8, IWHCS device 800 includes recirculation aperture 832, recirculation valve 882 and recirculation conduit 884. Recirculation aperture 832 is formed within chamber ceiling 132. Recirculation aperture 832 is adapted to recirculate water within sampling chamber 142. Recirculation aperture 832 facilitates the flow of water between sampling chamber 142 and recirculation conduit 884. Recirculation valve 882 is capable of opening and closing. Recirculation valve 882 is operatively coupled to chamber ceiling 132 and recirculation conduit 884. Recirculation valve 882 forms a watertight seal so that water does not flow between the exterior of sampling chamber 142 and the following: the interior of sampling chamber 142, recirculation aperture 832 and recirculation conduit 884. When recirculation valve 882 is open, water can flow between sampling chamber 142 and recirculation conduit 884 via recirculation aperture 832 given that the pressure differential is favorable for such flow.

As shown in FIG. 8, pump 770 is operatively coupled to recirculation conduit 884 via outtake valve 772. Pump 770 is capable of pumping water into or out of sampling chamber 142 via pump conduit 784 or recirculation conduit 884. Pump 770 is capable of creating a negative pressure within sampling chamber 142.

An exemplary operation of the closed-loop pump embodiment of IWHCS device 800 of FIG. 8 is now described with regard to a recirculation mode. In the exemplary operation of IWHCS device 800 in recirculation mode, IWHCS device 800 is situated flush against a boat hull (not shown in FIG. 8, however, shown in FIG. 1 as boat hull 198). Pressure is applied so that chamber sealing membrane 110 maintains contact with the boat hull, which prevents ambient water from entering sampling chamber 142. During simulated cleaning, pump 770 is activated with valves 772, 782 and 882 open. Thus, water within sampling chamber 142 is re-circulated through conduits 784 and 884.

An exemplary operation of the closed-loop pump embodiment of IWHCS device 800 of FIG. 8 is now described with regard to a negative pressure mode. In the exemplary operation of IWHCS device 800 in negative pressure mode, IWHCS device 800 is situated flush against a boat hull (not shown in FIG. 8, however, shown in FIG. 1 as boat hull 198). Pressure is applied so that chamber sealing membrane 110 maintains contact with the boat hull, which prevents ambient water from entering sampling chamber 142. Prior to simulating cleaning, pump 770 is activated to pull a small amount of water from sampling chamber 142 with intake valve 782 open and one or more of the following valves closed: outtake valve 772 and recirculation valve 882. Thus, a slight negative pressure is created within sampling chamber 142, which helps chamber sealing membrane 110 maintain a watertight seal. Then, simulated cleaning proceeds as described above with reference to the exemplary operation of IWHCS device 100 of FIG. 1.

Figure 9:
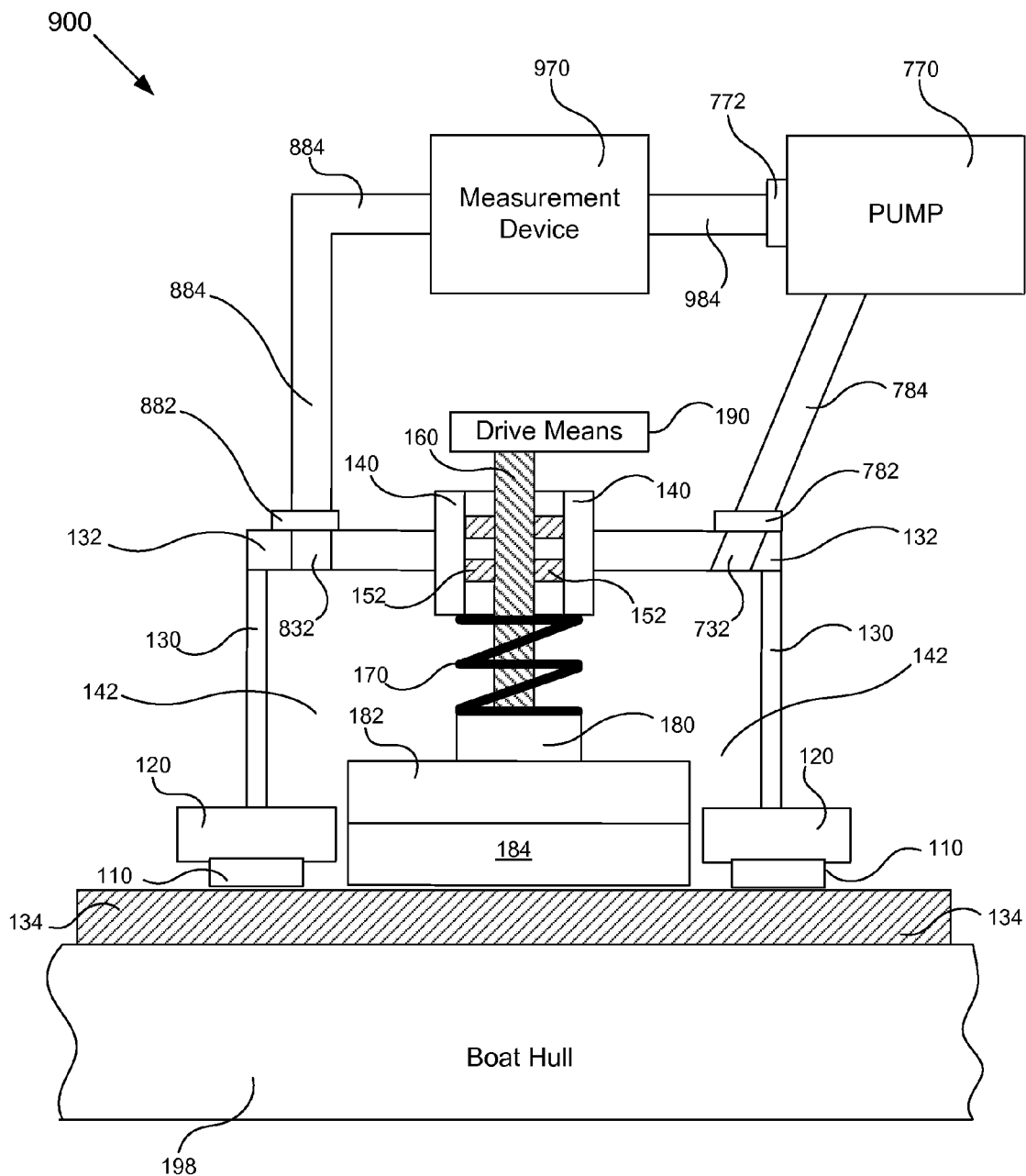
FIG. 9 is a side view of one embodiment of an in-water hull cleaning sampling device.

FIG. 9 is a side view of one embodiment of an in-water hull cleaning sampling device. FIG. 9 is a recirculation and measurement embodiment of the IWHCS device, which provides recirculation of water and measurement of contaminants contained within sampling chamber 142. The recirculation and measurement embodiment provides a convenient means for sampling and measuring water contaminants. IWHCS device 900 of FIG. 9 is substantially similar to IWHCS device 100 of FIG. 1 and IWHCS device 800 of FIG. 8, and thus, identical components are not described hereinagain.

As shown in FIG. 9, IWHCS device 900 includes measurement device 970 and measurement device conduit 984. Measurement device conduit 984 is operatively coupled to outtake valve 772. Measurement device conduit 984 is adapted to receive water from sampling chamber 142 via pump 770 and outtake valve 772. Measurement device 970 is operatively coupled to measurement device conduit 984 and recirculation conduit 884. Measurement device 970 is adapted to receive water from sampling chamber 142 via intake aperture 732, intake valve 782, pump conduit 784, pump 770, outtake valve 772 and measurement device conduit 984. Measurement device 970 is capable of analyzing the contents of water received from sampling chamber 142. Measurement device 970 comprises at least one sensor. Exemplary sensors include turbidity, salinity, oxygenation, acidity, mercury, copper, pesticide and bacterial. In one embodiment, measurement device 970 comprises a turbidity sensor. In one embodiment, measurement device 970 comprises electrodes. Measurement device 970 is also capable of transmitting measurement data or displaying measurement data. In one embodiment, measurement device 970 includes a data storage means such as RAM, ROM, hard disk, flash memory.

Figure 10:
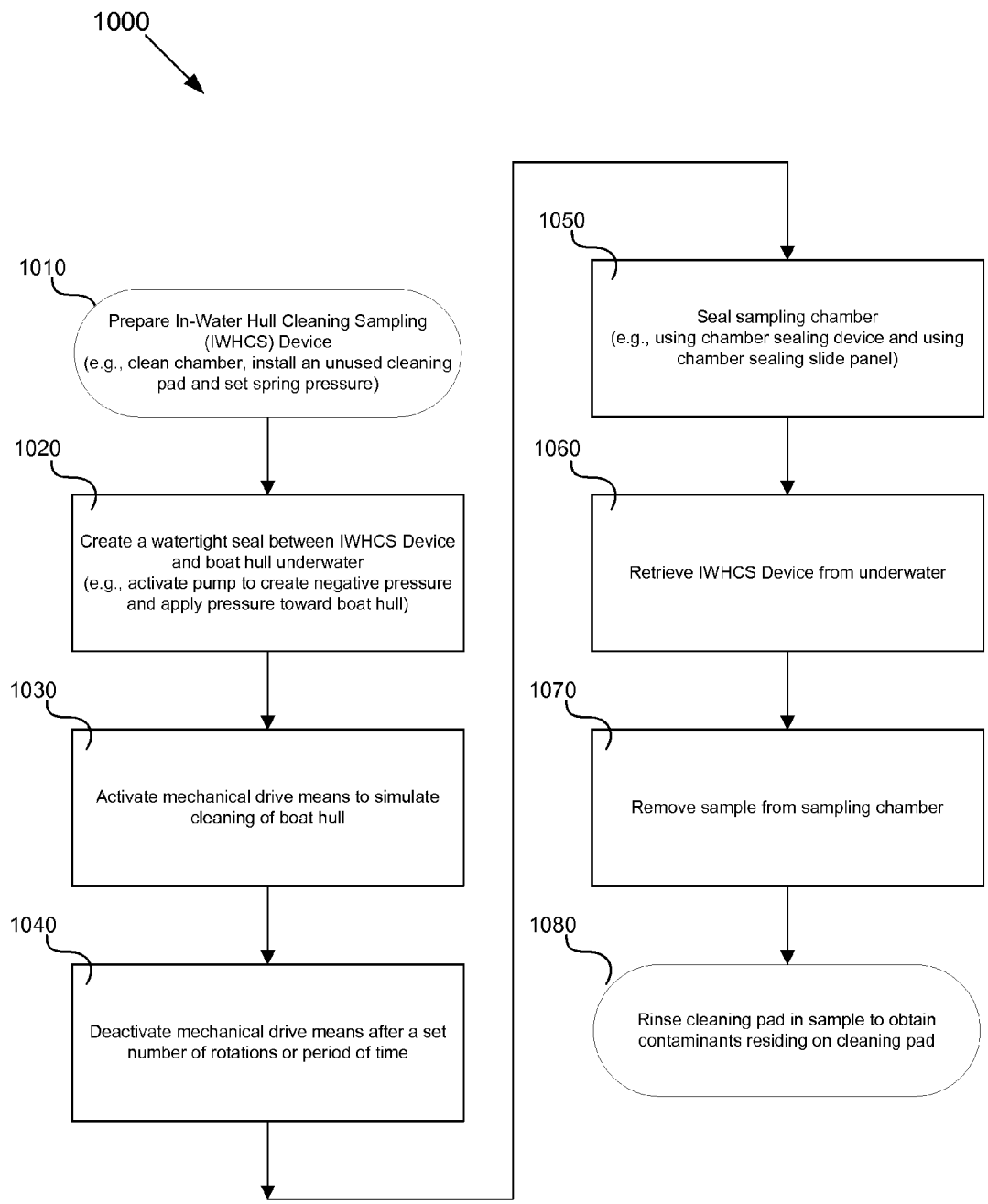
FIG. 10 is a flowchart of one embodiment of a method of an in-water hull cleaning sampling device.

FIG. 10 is a flowchart of one embodiment of a method of an in-water hull cleaning sampling device. As shown in FIG. 10, the method of flowchart 1000 includes steps 1010, 1020, 1030, 1040, 1050, 1060, 1070 and 1080, which comprise some of the procedures for one embodiment of a method of an in-water hull cleaning sampling device.

Step 1010 involves preparing the IWHCS device, such as devices 100, 200, 300, 400, 500, 600, 700, 800, or 900. For purposes of illustration, method 1000 will be discussed with primary reference to device 100 as described herein. As an example, step 1010 includes cleaning sampling chamber 142, installing an unused cleaning pad 184, and setting the spring pressure of pressure spring 170. Step 1020 involves creating a water-tight seal between the IWHCS device and the boat hull underwater. As an example, step 1020 involves activating a pump 770 (see FIG. 7) to create negative pressure and apply pressure towards boat hull 198. Step 1030 involves activating mechanical drive means 190 to simulate cleaning of boat hull 198. Step 1040 involves deactivating mechanical drive means 190 after a set number of rotations or a period of time.

Step 1050 involves sealing the sampling chamber. As an example, step 1050 may involve using chamber sealing device 110 or using a chamber sealing slide panel 440 (see FIG. 4) to seal sampling chamber 142. Step 1060 involves retrieving the IWHCS device from underwater. Step 1070 involves removing a sample from sampling chamber 142. Step 1080 involves rinsing cleaning pad 184 to obtain contaminants residing on the cleaning pad 184.

Figure 11:
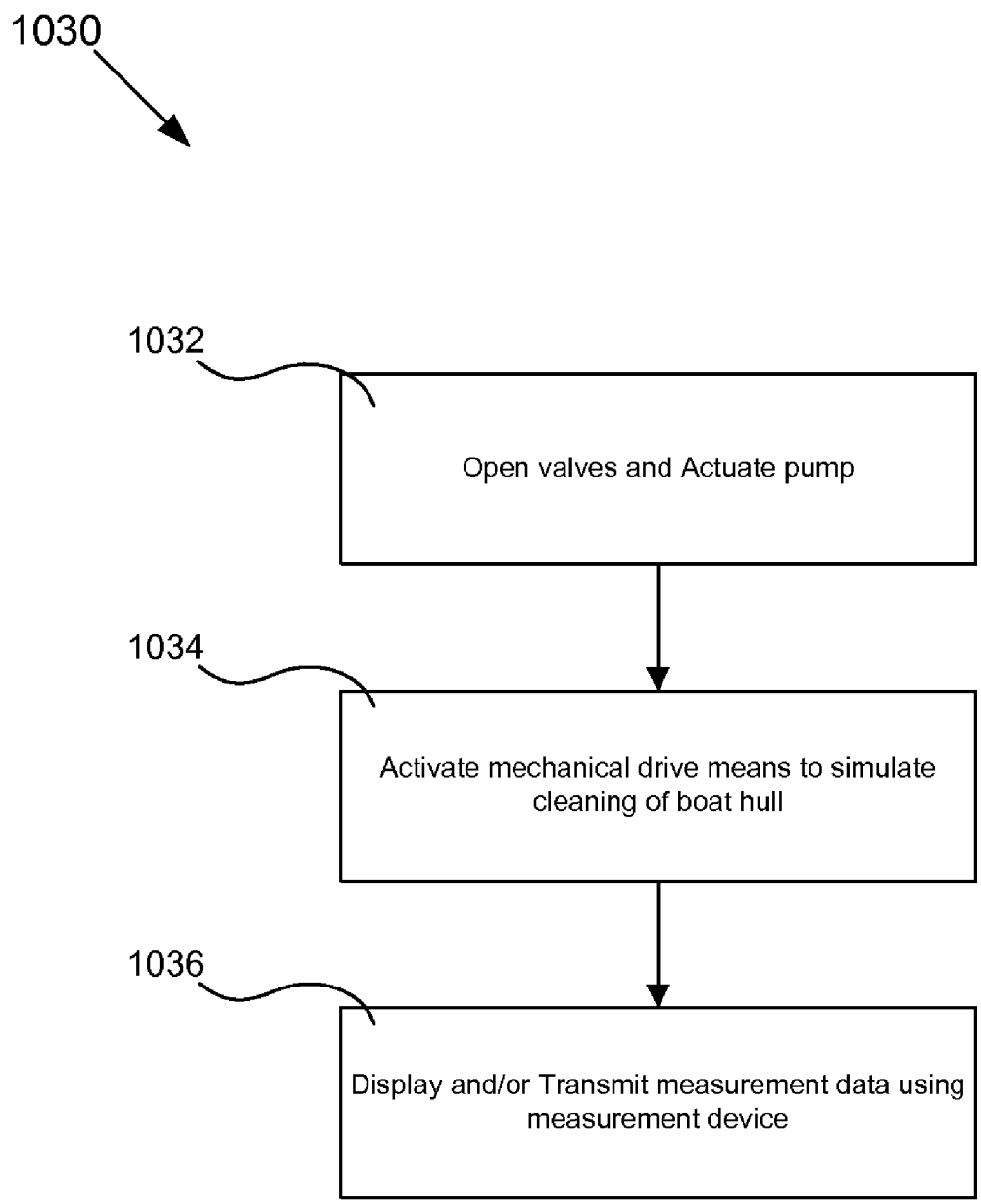
FIG. 11 is a flowchart of one embodiment of a method of an in-water hull cleaning sampling device.

FIG. 11 is a flowchart of one embodiment of step 1030 as discussed herein. As shown in FIG. 11, step 1030 may include steps 1032, 1034 and 1036. For purposes of illustration, step 1030 will be discussed with primary reference to device 700 as described herein. Step 1032 may involve opening a valve, such as intake valve 782, and actuating pump 770. Step 1034 involves activating mechanical drive means 190 to simulate cleaning of the boat hull (see FIG. 1). Step 1036 involves displaying and/or transmitting the measurement data using a measuring device, such as measuring device 302 shown in FIG. 3.

We claim:

1. An apparatus, comprising:
   a sampling chamber defined by a chamber sealing membrane, a base, a chamber wall and a chamber ceiling, wherein said sampling chamber is adapted to be watertight, wherein:
   said chamber sealing membrane is operatively coupled to said base;
   said base is operatively coupled to said chamber wall, and said chamber wall is operatively coupled to said chamber ceiling;
   a drive shaft housing, operatively coupled to said chamber ceiling in a watertight manner, wherein said drive shaft housing forms a concentric cylinder substantially centered upon a central longitudinal axis of said apparatus;
   a drive shaft sealing membrane, operatively coupled to said drive shaft housing in a watertight manner forming a concentric cylinder substantially centered upon said central longitudinal axis of said apparatus;
   a drive shaft, operatively coupled to said drive shaft sealing membrane, capable of rotating along said central longitudinal axis of said apparatus;
   a spring retainer, operatively coupled to said drive shaft, capable of retaining a spring;
   a pressure spring, operatively coupled to said drive shaft housing and said spring retainer, capable of simulating a desired pressure;
   a cleaning pad, operatively coupled to said drive shaft, capable of rotating in response to rotation of said drive shaft;
   a mechanical drive device, operatively coupled to said drive shaft, capable of providing a rotational force that rotates said drive shaft; and
   a chamber sealing device, operatively coupled to said sampling chamber, capable of providing a watertight seal between said sampling chamber and water outside of said sampling chamber.

2. The apparatus of claim 1, wherein said chamber sealing device comprises a substantially rigid, watertight material.

3. The apparatus of claim 1, wherein said cleaning pad comprises a stiff bristle brush.

4. The apparatus of claim 1, wherein said cleaning pad comprises a soft scouring pad.

5. The apparatus of claim 1, wherein said chamber ceiling comprises:
   a measurement device, operatively coupled to said sampling chamber, capable of analyzing the contents of said sampling chamber;
   a measurement device link, operatively coupled to said measurement device, capable of transmitting information from said measurement device; and
   a display, operatively coupled to said measurement device link, capable of receiving information from said measurement device via said measurement device link, and capable of displaying information.

6. The apparatus of claim 5, wherein said measurement device comprises a turbidity sensor.

7. The apparatus of claim 1, wherein said chamber sealing device comprises:
   an extended base, operatively coupled to said chamber wall and said sealing membrane;
   an extended base aperture, formed within and defined by said extended base; and
   a chamber sealing slide panel, operatively coupled to said extended base aperture, wherein said chamber sealing slide panel is adapted to allow said cleaning pad to simulate cleaning, and wherein said chamber sealing slide panel is adapted to form a watertight seal that encloses said sampling chamber when said cleaning pad is retracted into said sampling chamber.

8. The apparatus of claim 7, wherein said apparatus further comprises a base aperture formed within and defined by said base, wherein said base aperture is adapted to snugly house said chamber sealing slide panel to help form a watertight seal.

9. The apparatus of claim 1, wherein said chamber sealing device comprises:
   an extended base, operatively coupled to said chamber wall and said sealing membrane;
   an extended base aperture, formed within and defined by said extended base;
   a chamber sealing slide panel, operatively coupled to said extended base aperture, wherein said chamber sealing slide panel is adapted to allow said cleaning pad to simulate cleaning, and wherein said chamber sealing slide panel is adapted to form a watertight seal that encloses said sampling chamber when said cleaning pad is retracted into said sampling chamber; and
   a slide panel spring, operatively coupled to said chamber sealing slide panel and retained within said extended base aperture, capable of providing force to situate said chamber sealing slide panel in a watertight seal position.

10. The apparatus of claim 1, wherein said drive shaft further comprises:
    a drive shaft lock pin; and a drive shaft aperture, formed within and defined by said drive shaft, adapted to retain said drive shaft lock pin when said drive shaft aperture is situated above said drive shaft housing.

11. The apparatus of claim 1, wherein said base, said chamber wall and said chamber ceiling comprise a plastic material.

12. An apparatus, comprising:
a sampling chamber defined by a chamber sealing membrane, a base, a chamber wall, a chamber ceiling, wherein said sampling chamber is adapted to be watertight, wherein:
said chamber sealing membrane is operatively coupled to said base;
said base is operatively coupled to said chamber wall, and
said chamber wall is operatively coupled to said chamber ceiling;
a drive shaft housing, operatively coupled to said chamber ceiling in a watertight manner, wherein said drive shaft housing forms a concentric cylinder substantially centered upon a central longitudinal axis of said apparatus;
a drive shaft sealing membrane, operatively coupled to said drive shaft housing in a watertight manner forming a concentric cylinder substantially centered upon said central longitudinal axis of said apparatus;
a drive shaft, operatively coupled to said drive shaft sealing membrane, capable of rotating along said central longitudinal axis of said apparatus;
a spring retainer, operatively coupled to said drive shaft, capable of retaining a spring;
a pressure spring, operatively coupled to said drive shaft housing and said spring retainer, capable of simulating a desired pressure;
a cleaning pad, operatively coupled to said drive shaft, capable of rotating in response to rotation of said drive shaft;
a mechanical drive device, operatively coupled to said drive shaft, capable of providing a rotational force that rotates said drive shaft;
a chamber sealing device, operatively coupled to said sampling chamber, capable of providing a watertight seal between said sampling chamber and water outside of said sampling chamber;
an intake aperture, operatively coupled to and formed within said chamber ceiling, adapted to facilitate the flow of water from said sampling chamber;
an intake valve, operatively coupled to said chamber ceiling, capable of opening and closing and adapted to facilitate the flow of water from said intake aperture;
a pump conduit, operatively coupled to said intake valve, capable of facilitate the flow of water from said intake aperture;
a pump, operatively coupled to said pump conduit, capable of creating a negative or positive pressure within said sampling chamber when said intake valve is open or partially open, and capable of pumping water into or out of said sampling chamber via said pump conduit, said intake valve and said intake aperture; and
an outtake valve, operatively coupled to said pump, capable of opening and closing, capable of expelling water.

13. The apparatus of claim 12, wherein said apparatus further comprises:
a recirculation aperture, operatively coupled and formed within said chamber ceiling, adapted to facilitate the flow of water;
a recirculation valve, operatively coupled to said chamber ceiling, capable of opening and closing; and
a recirculation conduit, operatively coupled to said recirculation valve and said pump via said outtake valve, capable of facilitating the flow of water.

14. The apparatus of claim 12, wherein said apparatus further comprises:
a recirculation aperture, operatively coupled and formed within said chamber ceiling, adapted to facilitate the flow of water;
a recirculation valve, operatively coupled to said chamber ceiling, capable of opening and closing;
a recirculation conduit, operatively coupled to said recirculation valve, capable of facilitating the flow of water;
a measurement device conduit, operatively coupled to said pump via said outtake valve, capable of receiving water from said sampling chamber via said intake aperture, said intake valve, said pump conduit, said pump and said outtake valve; and
a measurement device, operatively coupled to said recirculation conduit, capable of analyzing the contents of water from said sampling chamber received via said measurement device conduit.

15. The apparatus of claim 14, wherein said measurement device is capable of transmitting measurement data.

16. The apparatus of claim 14, wherein said measurement device is capable of displaying measurement data.

17. The apparatus of claim 12, wherein said cleaning pad comprises a stiff bristle brush.

18. The apparatus of claim 12, wherein said cleaning pad comprises a soft scouring pad.

* * * * *